United States Patent [19]
Hendriksen et al.

[11] Patent Number: 5,463,157
[45] Date of Patent: Oct. 31, 1995

[54] PROCESS FOR PREPARING 3-METHYL-2-PENTENE

[75] Inventors: Dan E. Hendriksen, Kingwood, Tex.; Gerald G. McGlamery; Michael J. Keenan, both of Baton Rouge, La.; Derrick D. Pete, Missouri City, Tex.

[73] Assignee: Exxon Chemical Patents, Inc., Wilmington, Del.

[21] Appl. No.: 146,374

[22] Filed: Oct. 29, 1993

[51] Int. Cl.⁶ ............... C07C 2/04; C07C 2/26; C07C 2/34; C07C 2/24
[52] U.S. Cl. .......... 585/511; 585/510; 585/512; 585/638; 585/639; 585/640; 562/550; 562/551; 562/521
[58] Field of Search ............... 585/510, 511, 585/512, 638, 639, 640; 562/550, 551, 521

[56] References Cited

U.S. PATENT DOCUMENTS

| | | |
|---|---|---|
| 2,135,459 | 11/1938 | Loder . |
| 2,876,241 | 3/1959 | Koch et al. . |
| 3,099,687 | 7/1963 | Rohlffs et al. . |
| 3,167,585 | 1/1965 | Anderson et al. . |
| 3,262,954 | 7/1966 | Wehe, Jr. et al. . |
| 4,048,109 | 9/1977 | Ryu ........................... 585/511 |
| 4,101,600 | 7/1978 | Zhukov et al. . |
| 4,532,370 | 7/1985 | Le Quan et al. ............ 585/512 |
| 4,615,998 | 10/1986 | Le Quan et al. ............ 502/126 |
| 4,691,073 | 9/1987 | Michaelson ................. 585/639 |
| 5,037,997 | 8/1991 | Zhukov et al. ............. 585/512 |
| 5,118,871 | 6/1992 | Cikut et al. ................. 568/697 |
| 5,132,483 | 7/1992 | Schubert .................... 585/511 |

FOREIGN PATENT DOCUMENTS

| | | |
|---|---|---|
| 946327 | 1/1964 | United Kingdom . |
| 2140419 | 11/1984 | United Kingdom . |

OTHER PUBLICATIONS

Commereuc et al., "Dimerize Ethylene to Butene-1", *Hydrocarbon Processing*, Nov. 1984, pp. 118–120.

Primary Examiner—Sharon A. Gibson
Assistant Examiner—E. D. Irzinski
Attorney, Agent, or Firm—Richard D. Jordan

[57] ABSTRACT

A method for producing 3-methyl-2-pentene which is substantially free of any other $C_6$ olefin, except 2-ethyl-1-butene, by first producing a stream that contains 2-ethyl-1-butene from the trimerization of ethylene, and second by recovering the 2-ethyl-1-butene as 3-methyl-2-pentene via etherification, separation of the ether, and decomposition of the ether back to predominantly 3-methyl-2-pentene with some 2-ethyl-1-butene.

17 Claims, 3 Drawing Sheets

PROCESS FOR PREPARING 3-METHYL-2-PENTENE

The present invention relates generally to a method for producing 3-methyl-2-pentene via the trimerization of ethylene to yield a $C_6$ product which contains 2-ethyl-1-butene, followed by etherification of 2-ethyl-1-butene in the $C_6$ product, separation of the ether and decomposition of the ether to 3-methyl-2-pentene. This process is capable of producing 3-methyl-2-pentene, substantially free of all other $C_6$ olefins, except 2-ethyl-1-butene, which is useful for the preparation of 2-ethyl-2-methylbutanoic acid, a high-value neoacid.

BACKGROUND OF THE INVENTION

Researchers have been attempting for the past decade to develop an improved synthetic route to 2-ethyl-2-methylbutanoic acid (EMBA). The problem has been to develop an economically acceptable method for producing the olefin precursor, i.e., 3-methyl-2-pentene (3M2P) and/or 2-ethyl-1-butene (2E1B).

These olefin precursors are useful for the preparation of EMBA. However, the presence of even a few percent of any other $C_6$ olefin during preparation of this neoacid results in an unacceptable mixture of neoacids and neoacid esters that is exceedingly difficult to separate by distillation.

A number of refinery streams contain 3-methyl-2-pentene, but these streams contain many isomers of hexenes, and are not at all pure enough for the preparation of EMBA. 3-methyl-2-pentene may be produced from codimerizing ethylene with n-butenes over a supported sodium or potassium metal catalyst (see Soviet Union Patent No. 1,145,013 and Great Britain Patent No. 1,142,704), but these products also contain enough other isomers of hexene to make them unsuitable for the preparation of EMBA.

Mixed hexenes are produced as a by-product from the Alphabutol™ process (a trademark of the Institut Francais du Petrole), which is used to make 1-butene.

A typical analysis of mixed hexenes discharged from the Alphabutol™ process is set forth below:

| Component | Weight Percent |
|---|---|
| 3-methyl-1-pentene | 26.0 |
| 1-hexene | 6.5 |
| 2-ethyl-1-butene | 65.0 |
| Others (C6 + C8) | 2.5 |

This process is described in the November, 1984, issue of "Hydrocarbon Processing", pp. 118–120. Significantly, the only isohexene contained in the $C_6$ by-product of the Alphabutol™ process is 2-ethyl-1-butene. There are no 2-methylpentenes or 2,3-dimethylbutenes, and essentially no methylcyclopentenes. Although the $C_6$ by-product of the Alphabutol™ process does contain significant amounts of EMBA precursor olefins, the presence of other $C_6$ olefins results in EMBA product that is not of sufficient purity. Conventional fractional distillation of the mixed hexenes yields streams enriched in desirable hexenes, but these enriched hexene streams still do not yield satisfactory EMBA product.

Processes to recover isobutylene and isoamylene from mixed streams of $C_4$ or $C_5$ olefins are known. These involve selectively forming an ether from the isobutylene or isoamylene, separating the ether, and decomposing it back to the $C_4$ or $C_5$ iso-olefin plus alcohol. (See U.S. Pat. No. 4,691,073 (Michaelson), which issued on Sep. 1, 1987).

There is only one isomer of isobutylene and only one skeletal isomer of isoamylene. There are four skeletal isomers of isohexene, i.e., 2-methylpentene, 2,3-dimethylbutene, 1-methyl cyclopentene, and 3-methyl-2-pentene (or 2-ethyl-1-butene). All of these will react with an alcohol to form the respective ether.

The present inventors have developed a unique integrated process which combines the Alphabutol™ process or like processes with an etherification/decomposition process which recovers a $C_6$ iso-olefin to produce a 3-methyl-2-pentene product which is substantially free of all other $C_6$ olefins, except 2-ethyl-1-butene.

The present invention also provides many additional advantages which shall become apparent as described below.

SUMMARY OF THE INVENTION

A method for producing 3-methyl-2-pentene which is substantially free of any other $C_6$ olefin, with the exception of 2-ethyl-1-butene. This method comprises the steps of: (a) trimerizing an ethylene feedstream and/or co-dimerizing an ethylene and 1-butene feedstream in the presence of a titanium-based catalyst in order to form a hydrocarbon product comprising at least 2-ethyl-1-butene; (b) separating the hydrocarbon product from the catalyst; (c) etherifying the hydrocarbon product to form an ether-containing stream; (d) separating an ether product from the ether-containing stream; (e) decomposing the ether product to form a 3-methyl-2-pentene stream; and (f) separating an alcohol and unreacted ether product from the 3-methyl-2-pentene stream to form a 3-methyl-2-pentene product.

Optionally, an additional step of separating a $C_6$ product which contains 2-ethyl-1-butene from the hydrocarbon product of step (b) and etherifying the $C_6$ product in step (c) instead of the hydrocarbon product may be employed in accordance with the present invention.

Trimerization and/or co-dimerization step (a) is preferably conducted at a temperature in the range between about 0° C. to about 100° C., more preferably between about 50° C. to about 60° C. Trimerization and/or co-dimerization step (a) is also preferably conducted at a pressure sufficient to maintain the ethylene or ethylene and 1-butene in the liquid phase, i.e., a pressure in the range between about 0.2 to about 30 atm ($2.026 \times 10^4$ N/m$^2$ to $3.0398 \times 10^6$ N/m$^2$).

Catalyst separation step (b) is carried out in an adsorption column or by simply distilling the hydrocarbon product away from the essentially non-volatile catalyst components.

The optional hydrocarbon separation step is carried out in a fractionation device. The preferred fractionation device comprises a first distillation column which is capable of separating the unreacted ethylene from 1-butene and heavier olefins and a second distillation column which is capable of separating 1-butene from a $C_6$ and heavier olefins product. A more preferred fractionation device comprises a first distillation column which is capable of separating the unreacted ethylene from 1-butene and heavier olefins, a second distillation column which is capable of separating 1-butene from $C_6$ and heavier olefins, and a third distillation column which is capable of separating a $C_6$ product from $C_8$ and heavier olefins.

Etherification step (c) comprises the following steps: (i)

supplying the hydrocarbon product and at least one alcohol, e.g., methanol, to a reactor to produce an etherification mixture; and (ii) catalytically reacting the etherification mixture in the reactor containing an etherification catalyst under reaction conditions which favor forming an ether-containing stream from the hydrocarbon product and alcohol.

Ether separation step (d) comprises the feeding of the ether-containing stream into a distillation column. It is preferable that the distillation column has a catalytic distillation reaction zone including an acid resin catalyst to improve conversion of olefin to ether. Otherwise, unreacted olefin and methanol can be recycled to the etherification reactor to improve conversion.

Decomposition step (e) comprises contacting of the ether product with at least one catalyst selected from the group consisting of: acid resin catalysts, zeolite catalysts, alumina catalysts, and clay catalysts, especially hydrofluoric acid treated attapulgite clay catalysts (sold by Engelhard as D-5206G).

Separation step (f) comprises the feeding of the 3-methyl-2-pentene stream to extraction and distillation columns wherein alcohol and unreacted ether product are separated from the 3-methyl-2-pentene stream.

The present invention also pertains to a method for producing 2-ethyl-2-methylbutanoic acid which comprises the steps of: (i) producing 3-methyl-2-pentene which is substantially free of any other $C_6$ olefin, except 2-ethyl-1-butene, which comprises the steps of: (a) trimerizing an ethylene feedstream and/or co-dimerizing an ethylene and 1-butene feedstream in the presence of a titanium-based catalyst in order to form a hydrocarbon product comprising at least 2-ethyl-1-butene; (b) separating the hydrocarbon product from the catalyst; (c) etherifying the hydrocarbon product to form an ether-containing stream; (d) separating an ether product from the ether-containing stream; (e) decomposing the ether product to form a 3-methyl-2-pentene stream; and (f) separating an alcohol and unreacted ether product from the 3-methyl-2-pentene stream to form a 3-methyl-2-pentene product; and (ii) mixing the 3-methyl-2-pentene product together with carbon monoxide, water, and a strong acid catalyst at a temperature of about 25° C. to about 100° C. and at a pressure in the range between about 1000 psig ($6.996 \times 10^6$ N/m$^2$) to about 3000 psig ($2.0786 \times 10^7$ N/m$^2$) to form 2-ethyl-2-methylbutanoic acid.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
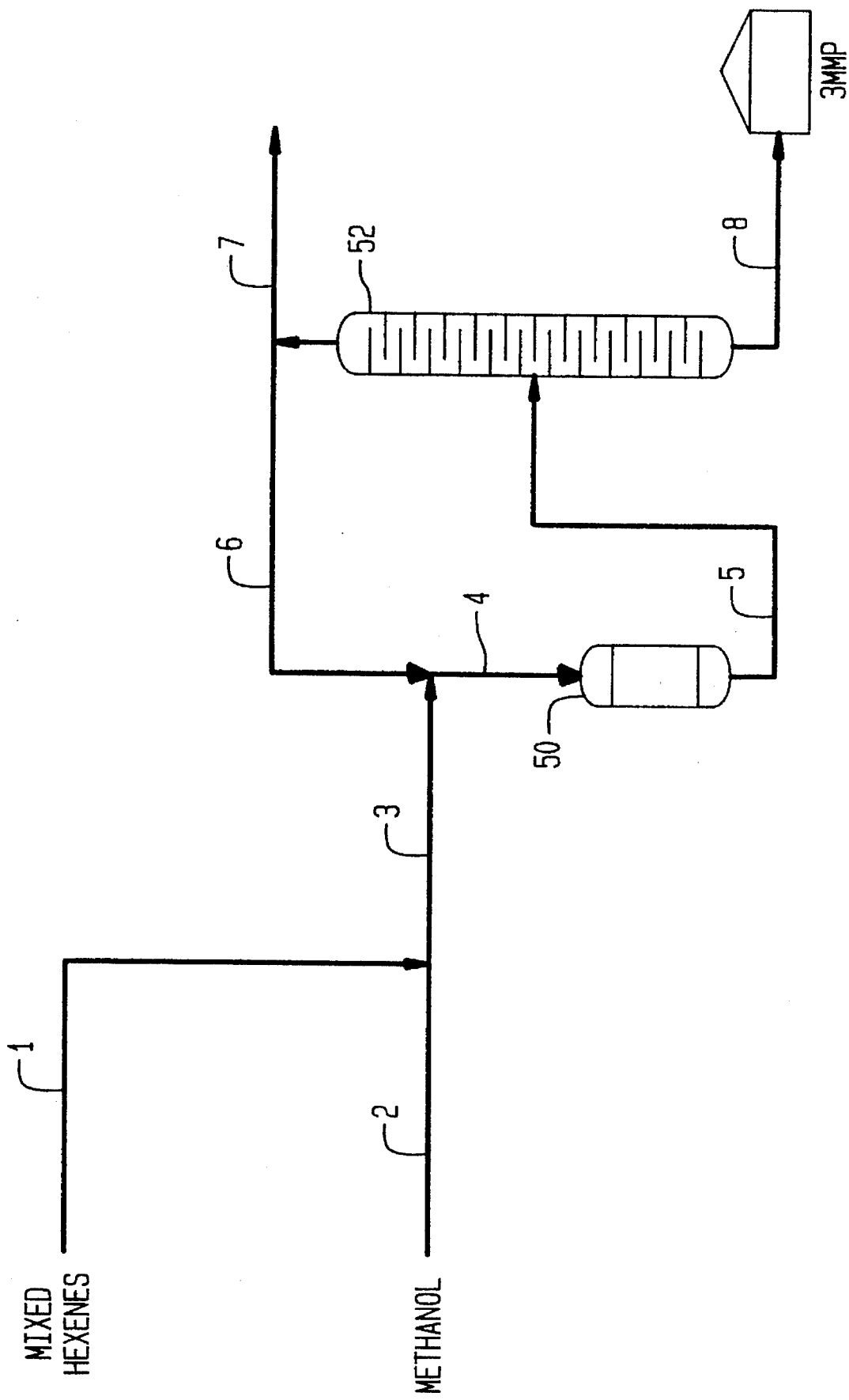
FIG. 1 illustrates the process flow diagram for the synthesis of 3-methoxy-3-methylpentane according to the present invention.

The present invention involves the unique integration of two processes to produce a 3-methyl-2-pentene product which is substantially free of all other olefins, especially $C_6$ olefins, except 2-ethyl-1-butene. The first process involves the preparation of an olefin stream containing 2-ethyl-1-butene, with no other $C_6$ iso-olefins such as 2-methylpentene. The second process involves the recovery of this 2-ethyl-1-butene from the olefin stream via etherification to 3-methoxy-3-methylpentane, separation of the ether, and decomposition of the ether back to 3-methyl-2-pentene.

The reactions to produce 2-ethyl-1-butene from ethylene, or ethylene and 1-butene, are set forth below in equations 1 and 2.

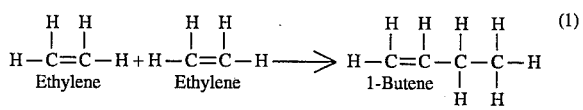

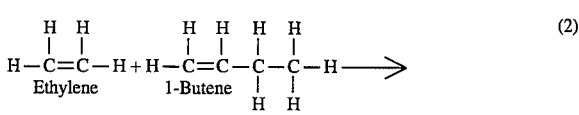

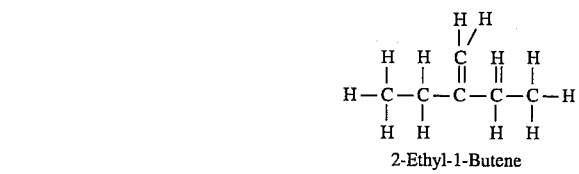

2-Ethyl-1-Butene

One process that uses these reactions was developed by Institut Francais du Petrole, and is known as the Alphabutol™ process. This process is used to prepare 1-butene by dimerizing ethylene. The $C_6$ olefins produced are considered by-products. The isohexene 2-ethyl-1-butene is a major $C_6$ product. By the nature of how they are produced, there are no other $C_6$ iso-olefins in this stream of $C_6$ olefins produced from ethylene.

The Alphabutol™ process uses a homogeneous catalyst which means that reactants, products and catalyst are all soluble in the same liquid phase. This catalyst is preferably a titanium-based catalyst.

The Alphabutol™ process is described in detail in Commereuc et al., "Dimerize Ethylene to Butene-1," *Hydrocarbon Processing*, November 1984, pp. 118–120. This is a simple process which is characterized by:

"(1) low operating temperature (50° to 60° C.) requiring no heating medium for the reaction section; (2) low operating pressure sufficient only to maintain the reactants in the liquid phase; (3) no solvent requirement; and (4) no sophisticated materials requirement (only carbon steel is needed as a material of construction).

The process involves the feeding of polymer-grade ethylene, which is assumed available in the vapor phase, to a liquid phase reactor through a distributor. The dimerization reaction occurs in the liquid phase due to the specific catalyst which is continuously metered into the reactor solution. The heat of reaction is removed outside the reactor by a classical pump-around system, equipped with an air or water cooler. The product from the reactor is withdrawn from the bottom section as a liquid containing the spent catalyst.

The spent catalyst is then removed from the effluent and sent to disposal, e.g. incineration, while the hydrocarbons are routed to the fractionation section. In this section, the first tower separated the unconverted ethylene for recycle to the reactor, and a second column produces the pure butene-1 overhead and the oligomers (predominantly $C_6$ olefins) as bottoms."

Another process for synthesizing 1-butene by dimerization of ethylene and which also results in trimerization to 2-ethyl-1-butene is set forth in U.S. Pat. No. 4,101,600 (Zhukov et al.), which issued on Jul. 18, 1978, and which is incorporated herein by reference. Two patents which are related to the Alphabutol™ process and which are assigned to Institut Francais du Petrole are U.S. Pat. Nos. 4,532,370 (Le Quan et al.), which issued on Jul. 30, 1985, and 4,615,998 (Le Quan et al.), which issued on Oct. 7, 1986. This later patent discloses a catalyst formed by reacting, in a hydrocarbon medium, a trialkyl-aluminum with a mixture of an alkyl titanate and an ether. Both of these patents are also incorporated herein by reference.

Processes to recover isobutylene and isoamylene from mixed streams of $C_4$ or $C_5$ olefins are known. These involve selectively forming an ether from the isobutylene or isoamylene, separating the ether, and decomposing it back to the $C_4$ or $C_5$ iso-olefin plus alcohol. (See U.S. Pat. No. 4,691,073 (Michaelson), which issued on Sep. 1, 1987).

The present inventors have utilized etherification to recover 2-ethyl-1-butene as the isomerized 3-methyl-2-pentene in accordance with the following reaction:

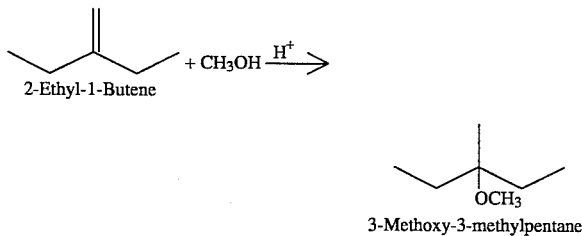

After this ether is separated by distillation from the unreacted hydrocarbons, 3-methyl-2-pentene is produced by decomposition of the ether in accordance with the following reaction:

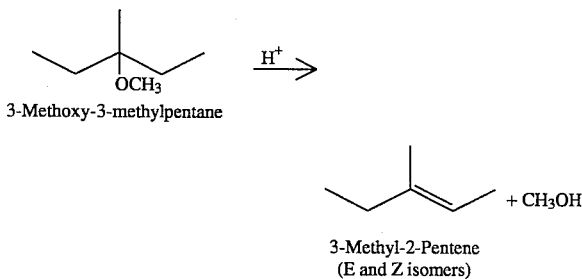

The 3-methyl-2-pentene is produced predominantly in the ether decomposition step because it is thermodynamically more stable than the 2-ethyl-1-butene.

The present invention involves the feeding of a mixture containing 2-ethyl-1-butene and methanol into the feed zone of a reactor (i.e., a fixed-bed guard reactor), and contacting the resultant mixture of 2-ethyl-1-butene and methanol with a fixed bed acidic cation exchange resin (e.g., Amberlyst® 15) in the reaction zone, thereby catalytically reacting the 2-ethyl-1-butene with the methanol under conditions which favor forming the resultant 3-methoxy-3-methylpentane.

Where the etherification step of the present invention is practiced in a catalytic distillation process, the catalytic material may be in any form which permits its incorporation into a distillation tower, such as a fixed bed, but may also be in a form which serves as a distillation packing, for example, rings, saddles, balls, irregular pieces, sheets, tubes, spirals, packed in bags, plated on grills or screens, and reticulated polymer foams.

Catalysts which have been found to be suitable for use in the etherification step of the present invention are resin catalysts such as cation exchange resin catalysts, acidic resin catalysts, macroreticular sulfonic acid cation exchange resin catalysts, and solid acid catalysts. Still others have used a zeolite as an etherification catalyst. Preferred catalysts for purposes of the present invention, however, are acid catalysts, such as acidic resin catalysts. A more preferred catalyst for purposes of the present invention is a macroreticular sulfonic acid cation exchange resin such as a sulfonated copolymer of polystyrene-divinylbenzene. Such catalysts include Amberlyst® 15 and 15C (marketed by Rohm and Haas), Lewatit SPC 118 and SPC 118 BG (marketed by Miles/Bayer), and Dowex M-31 and M-32 (marketed by the Dow Chemical Co.). A special version of this type of catalyst, i.e., Dowex DR-2040 (marketed by the Dow Chemical Co., is used specifically for reactive distillation.

The catalyst for the ether decomposition can be a solid acid such as an acid cation exchange resin, a clay, particularly hydrofluoric acid-treated attapulgite clay (sold by Engelhard as D-5206G), a zeolite compound or alumina. The zeolite catalyst is preferably a calcium Y zeolite as set forth in U.S. Pat. No. 5,254,785.

Figure 2:
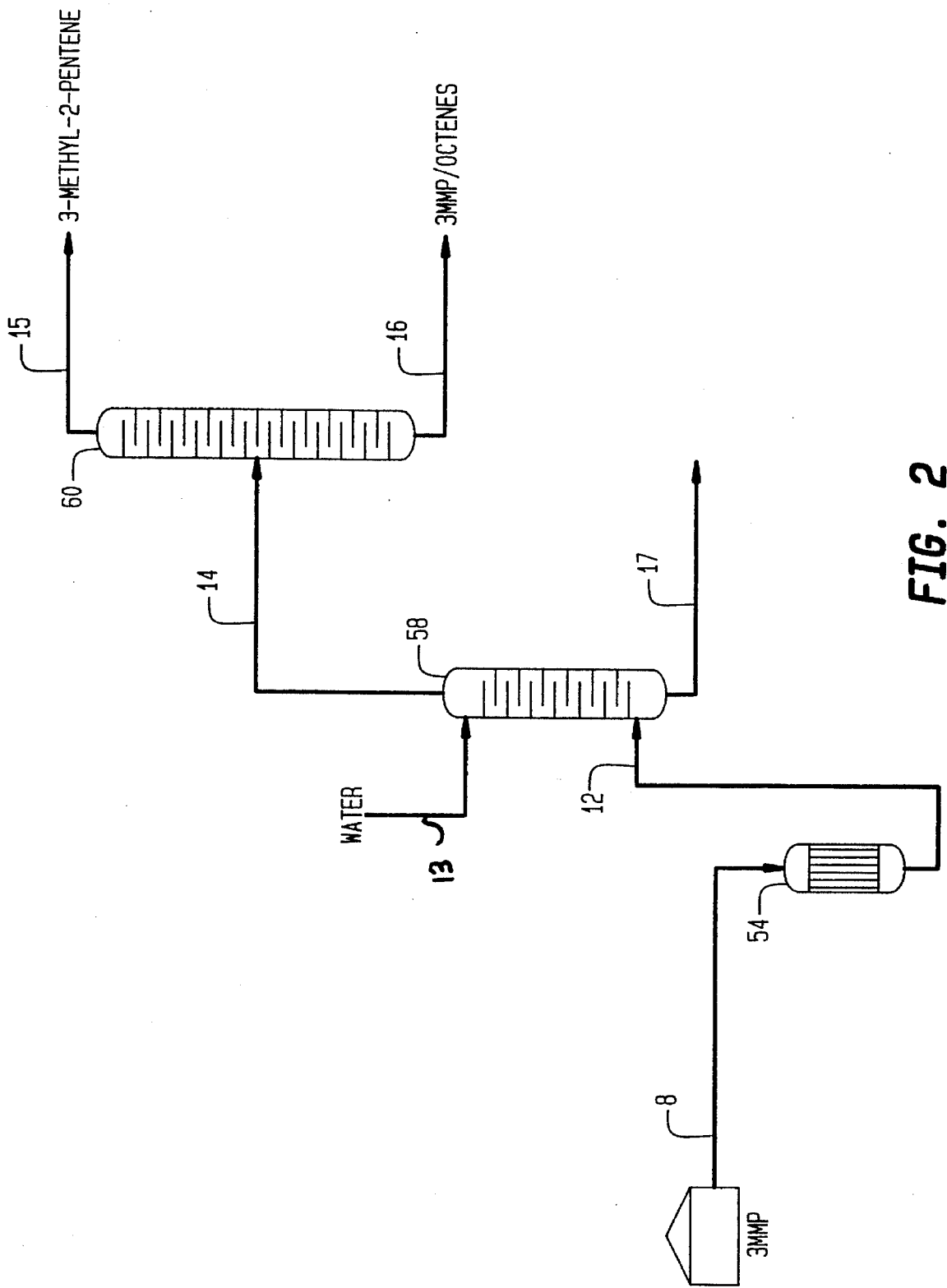
FIG. 2 illustrates the process flow diagram for the recovery of 3-methyl-2-pentene from 3-methoxy-3-methylpentane according to the present invention.

Referring now to FIGS. 1 and 2, a schematic system is shown which can be used to recover 3-methyl-2-pentene.

A feedstream 1 of mixed hexenes produced from the Alphabutol™ process or its equivalent is mixed with a feedstream 2 of methanol. The mixture of hexenes and methanol are sent to etherification reactor 50 via conduits 3 and 4. The etherification reactor 50 is provided with an acidic resin catalyst, such as Amberlyst® 15 and 15C, Lewatit SPC 118 and SPC 118 BG, and Dowex M-31 and M-32, and is heated to an appropriate temperature (i.e., preferably 72° C. to 78° C. (130°–140° F.)) and maintained at a pressure sufficient to keep the reactants in the liquid phase. The ether-containing stream 5 leaving reactor 50 is composed of 3-methoxy-3-methylpentane (3MMP), unreacted hydrocarbons and methanol ($CH_3OH$). Ether-containing stream 5 is then fed to a distillation column 52. The overhead stream from distillation column 52 is composed of a raffinate which is depleted in 2-ethyl-1-butene. A portion of the raffinate may optionally be recycled to reactor 50 via conduit 6 to improve conversion. The raffinate is passed through methanol removal and final clean-up procedures via conduit 7. The bottoms stream 8 from distillation tower 52 contains 3MMP in admixture with hydrocarbons boiling higher than hexenes (if present). This stream 8 is passed to a decomposition reactor 54 wherein it is contacted with either an acidic resin catalyst, a clay catalyst, a zeolite catalyst, or an alumina catalyst at a preferred temperature of about 325° F. (180° C.) and a pressure in the range between about 10 to 30 psig ($1.7027 \times 10^5$ N/m$^2$ to $5.1082 \times 10^5$ N/m$^2$) to form a 3-methyl-2-pentene stream. This 3-methyl-2-pentene stream is then sent via conduit 12 from decomposition reactor 54 to countercurrent extraction means 58, wherein water is added via conduit 13. The methanol and water are removed as bottoms via conduit 17. 3-Methyl-2-pentene, residual 3MMP ether, and heavy olefins (if present) are taken overhead via conduit 14 and sent to a distillation column 60, wherein 3-methyl-2-pentene is separated from the residual 3MMP and heavy olefins.

Figure 3:
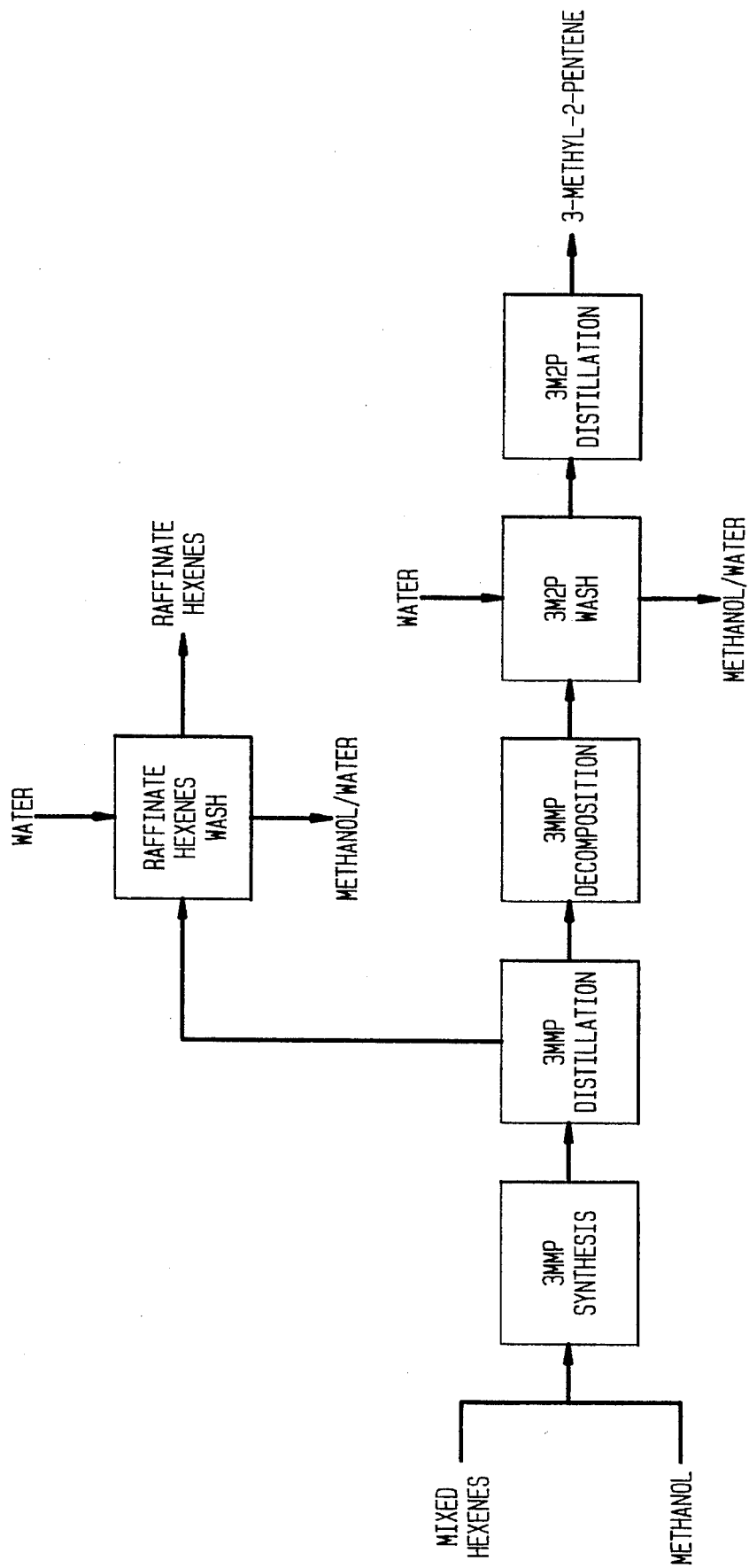
FIG. 3 is a block diagram which depicts both the synthesis of 3-methoxy-3-methylpentane and recovery of 3-methyl-2-pentene according to the present invention.

A block diagram for recovering 3-methyl-2-pentene from mixed hexenes and methanol according to the present invention is shown in FIG. 3.

The 3-methyl-2-pentene compound produced in accordance with the above method steps is substantially free of all other C6 olefins, except 2-ethyl-1-butene and is particularly useful in the preparation of 2-ethyl-2-methylbutanoic acid (EMBA). The 2-ethyl-2-methylbutanoic acid is a known commodity useful as an intermediate in the preparation of various herbicides. European Patent Specification No. 81304225.6 discloses herbicides which may be prepared from 2-ethyl-2-methylbutanoic acid.

2-Ethyl-2-methylbutanoic acid is preferably synthesized by reacting 3-methyl-2-pentene, 2-ethyl-1-butene, or a mixture thereof with carbon monoxide in the presence of an acid catalyst, followed by addition of water to the catalyzed product. This synthesis process provides an unusually high yield of the 2-ethyl-2-methylbutanoic acid product, especially when 3-methyl-2-pentene is carbonylated in the presence of an acid catalyst, preferably a strong acid catalyst, followed by reaction with water. Furthermore, only one $C_7$ by-product, i.e., 2,2-dimethylpentanoic acid, is formed in any significant amount (i.e., about 3–4 weight %) and conversion of the olefins is essentially quantitative.

Small portions of non-$C_7$ by-product acids are separable by distillation. Separation of $C_7$ acid isomers is difficult and typically requires superfractionation. Separation of hexyl alcohol esters of $C_7$ acids is also difficult and typically requires superfractionation. The importance of the invention is in providing 2-ethyl-2-methylbutanoic acid as the predominant $C_7$ isomer with little or no contamination by $C_{13}$ esters.

The process for synthesizing 2-ethyl-2-methylbutanoic acid is preferably carried out in a closed reactor under a pressure of carbon monoxide and preferably at elevated temperature. Any pressure and temperature may be used so long as the concentration of carbon monoxide present and the temperature of the reaction is sufficient to bring about conversion of the olefin reactant in the feedstream to the desired product, i.e., 2-ethyl-2-methylbutanoic acid. The temperature may range from a low temperature where the reaction will progress very slowly up to a high temperature wherein either the catalyst, materials, reactants, or products are destroyed by decomposition or other reaction. Suitable reaction temperatures range upwardly from at least about 25° C. For reactions with most of the acids which are effective as catalysts in the synthesis of 2-ethyl-2-methylbutanoic acid and for most carbon monoxide partial pressures, the reaction should generally be carried out at temperatures no higher than about 72°–82° C. This temperature range usually prevents decomposition of the catalyst material.

The synthesis of 2-ethyl-2-methylbutanoic acid may be carried out over a broad range of pressures so long as the desired end product is obtained from an olefin reactant of the feed. The range of pressures for the synthesis may vary broadly so long as the carbon monoxide is made available to the olefin reaction for formation of the desired product in the closed reactor.

An autoclave type reactor is suitable for preparation of the 2-ethyl-2-methylbutanoic acid. Mixtures of gases may be used to pressurize the reactor so long as a significant portion of the overall gas pressure is attributable to the carbon monoxide reactant. Gases which would interfere with or compete with the carbonylation should be avoided. Preferably, the reaction gas is at least about 50 weight percent carbon monoxide, more preferably 80–90 weight percent carbon monoxide and most preferably substantially entirely (100%) carbon monoxide. Suitable reaction pressures will range upwardly from 500 psig ($3.549 \times 10^6$ N/m$^2$) carbon monoxide partial pressure to an upper limit which is generally determined by the capabilities of the reaction vessel. Preferably, a stainless steel or a similar vessel is used to avoid problems with the acid catalyst, and pressures available for operation of the process will then depend upon the capabilities of the reactor. A good operating range for the synthesis of 2-ethyl-2-methylbutanoic acid is above 1,200 psig ($8.375 \times 10^6$ N/m$^2$) carbon monoxide partial pressure. A desirable operating pressure is above 3,000 psig ($2.0938 \times 10^7$ N/m$^2$) if the equipment is suitable for such high pressures.

Diluents including inert paraffinic solvents such as heptane or hexane may be used and may in fact improve selectivity somewhat. However, they are not required according to the invention. Diluent or solvent portions of the acid catalyst may be used and reused for the reaction.

The preferred synthesis involves the reaction of a 3-methyl-2-pentene olefin feed with carbon monoxide in the presence of an acid catalyst, followed by contact, reaction, or "quenching" with water to provide the desired 2-ethyl-2-methylbutanoic acid in high yield. Those acids generally classified as strong acids are preferred, strong inorganic acids being more preferred catalysts. Use of concentrated acids is also preferred. Suitable acids for reaction with the olefins include sulfuric acid, phosphoric acid, hydrochloric acid, boron trifluoride dihydrate, and other acids in this family or those of another type which bring about the conversion of the $C_6$ branched olefin to the 2-ethyl-2-methylbutanoic acid.

After the $C_6$ branched olefin in the reaction feed is contacted with an acid and carbonylated, the reaction product is quenched or otherwise contacted with water to form the 2-ethyl-2-methylbutanoic acid. It has been found that phosphoric acid has the best reactivity with the $C_6$ branched olefins, but phosphoric acid, like sulfuric acid, has a high corrosivity problem. Accordingly, a good compromise acid, where required for the synthesis of 2-ethyl-2-methylbutanoic acid is boron trifluoride dihydrate ($BF_3 \cdot 2H_2O$).

In the water addition step, solutions of water may also be used so long as the other ingredients in the solution do not interfere with the recovery of the 2-ethyl-2-methylbutanoic acid.

The preferred neoacid synthesis process comprises reacting one mole part of 3-methyl-2-pentene and/or 2-ethyl-1-butene at an effective temperature and carbon monoxide pressure in the presence of an acid followed by contacting the reaction mixture with water, preferably in excess, so as to form the desired 2-ethyl-2-methylbutanoic acid product in high yield. The carbon monoxide pressure in the reactor may be started at a sufficiently high level or with a sufficiently large over-pressure space that, during the course of the reaction, the amount of carbon monoxide is not significantly depleted. Alternatively, the carbon monoxide pressure may be maintained at a desired level or otherwise varied by supplying additional carbon monoxide or carbon monoxide-containing gas mixture to the reactor during the course of the reaction. Preferably, the carbon monoxide is bubbled through the bottom of the reactant liquid olefin mixture.

The amount of acid used depends upon the strength of the acid, i.e., the type of acid used and the concentration of the acid. Generally, for each mole part of reactant olefin(s) at least about 1.0 mole part of acid is used. The acid catalyst is preferably used in excess since it is recovered. About 1.0 to 2.0 mole parts is usable, preferably about 1.0 to 1.5, more preferably about 1.0 to 1.1 mole parts. Larger amounts of acid may be used as diluent. The more limited range for the acid catalyst to conserve resources on a commercial scale is about 1 to 1.1 mole parts of acid per mole part of reactant olefin. Alternatively, large acid/olefin ratio reactions may be conducted and the acid recycled.

EXAMPLE 1

The following example illustrates a laboratory method for recovery of 3-methyl-2-pentene (containing some 2-ethyl-1-butene).

The solid acid catalyst used in both ether synthesis and decomposition is Amberlyst® 15, a macroreticular ion exchange resin in the acid form. The Amberlyst® 15 was washed with distilled water until the washes were colorless, and then dried in an oven overnight at 110° C. A mixture of $C_6$ olefins obtained as a by-product from the Alphabutol™ process was analyzed by gas chromatography, and a 10% molar excess of methanol over the analyzed 2-ethyl-1-butene content was added. Dry Amberlyst® 15 was added to this mixture and the slurry was stirred at room temperature until about half of the 2-ethyl-1-butene was converted to an ether, i.e., 3-methoxy-3-methylpentane. (This conversion is limited by equilibrium). The solid acid resin was removed by filtration and the unreacted methanol was removed by washing four times with distilled water. The resulting mixture of ether and hydrocarbon was distilled, and a heartcut of ether was obtained. The isolated ether was then decomposed back to olefin and methanol. This was done by adding dry Amberlyst® 15 to the ether, heating, and distilling off the olefin and the methanol as they were formed. The collected material was washed several times with distilled water to remove the methanol, and was then distilled one more time (from added xylenes to avoid distillation to dryness). The product purity was 99.9% of the desired two olefins, i.e., 5.01% 2-ethyl-1-butene and 94.90% 3-methyl-2-pentene (two isomers).

EXAMPLE 2

A mixture of $C_6$ olefins (including some heavier olefins) obtained as a by-product of the Alphabutol™ process was mixed with technical grade methanol and fed to a series of three tubular reactors. Each reactor was nominally 1 inch (2.54 cm) in diameter and 20 feet (6.096 m) in length, and each was packed with Dowex® M-31 ion exchange resin. The reactors were maintained at temperatures in the range between 110° F. (61.1° C.) to 150° F. (83.3° C.). Mass flow rates to the reactor train were varied from 33 to 39 $lb_m$/h (14.97 to 17.69 $kg_m$/h). The molar ratio of methanol to 2-ethyl-1-butene was varied from 1.1 to 1.3. Reactor train outlet pressure was maintained at 20 psig ($2.392 \times 10^5$ $N/m^2$).

The effluent from the synthesis reactors was then distilled in a 6 inch (15.24 cm) diameter fractionation column containing 50 feet (15.24 m) of packing. Methanol and unreacted hexenes were taken as an overhead stream, while 3-methoxy-3-methylpentane and heavy olefins were taken as a bottom stream.

The 3MMP and heavy olefins stream was then fed to a 1 inch (2.54 cm) diameter, 20 feet (6.096 m) long, tubular reactor. The reactor was packed with either granular, hydrofluoric acid-treated clay, or with calcium Y zeolite extrudate. For the HF-treated clay, reactor temperatures were varied between 300° and 375° F. (167° to 208° C.), and mass flow rates were varied from 9.7 to 11.7 $lb_m$/h (4.4 to 5.3 kg/h). For the calcium Y zeolite, reactor temperatures were varied between 300 and 350° F. (166.7° to 194.4° C.), and mass flow rates were varied from 13.8 to 19.3 $lb_m$/h (6.26 to 8.75 kg/h). Reactor outlet pressure was maintained at 5 to 10 psig ($1.358 \times 10^5$ to $1.703 \times 10^5$ $N/m^2$).

The resulting product was washed in a four-stage, cross-current, mixer-settler extraction with water used to remove methanol. The product was then distilled in a 3 inch (7.62 cm) diameter fractionation column containing 44 feet (13.4 m) of packing. The 3-methyl-2-pentene and 2-ethyl-1-butene were taken as an overhead stream, while the unreacted 3MMP and heavy olefins were taken as a bottom stream.

The final product, when analyzed by gas chromatography, had the composition set forth below in Table 1:

TABLE 1

| (Composition of 3-Methyl-2-Pentene Final Product) | |
| --- | --- |
| Component | Weight Percent |
| 2-ethyl-1-butene | 10.30 |
| 3-methyl-2-pentene (E & Z) | 89.24 |
| other hydrocarbon | 0.46 |

EXAMPLE 3

A sample of 3-methyl-2-pentene concentrate was prepared in accordance with the steps of Example 1. The composition of the material, as measured by gas chromatography, is shown in Table 2.

TABLE 2

| (Composition of 3-Methyl-2-Pentene Concentrate) | |
| --- | --- |
| Component | Weight Percent |
| 2-ethyl-1-butene | 5.01 |
| 3-methyl-2-pentene (E & Z) | 94.90 |
| other hydrocarbon | 0.09 |

A 400 mL quantity of the 3-methyl-2-pentene concentrate was added to a 1 liter autoclave reactor. The reactor agitator was started, and the reactor was pressurized to 1300 psig ($9.0645 \times 10^6$ $N/m^2$) with carbon monoxide. Over a period of 160 minutes, 300 mL of $BF_3 \cdot 2H_2O$ were added to the reactor so that the final reactor pressure was 1500 psig ($1.03 \times 10^7$ $N/m^2$). At the end of this period, the addition of $BF_3 \cdot 2H_2O$ was stopped, and the contents were allowed to mix for another 300 minutes. During the reaction, the reactor contents were maintained at a temperature of 52° C.

At the end of 300 minutes, the reactor contents were washed with water to remove the catalyst. The resulting product had the component make-up as set forth below in Table 3.

TABLE 3

| (3-Methyl-2-Pentene Concentrate Carbonylation Reactor Product) | |
| --- | --- |
| Component | Weight Percent |
| olefins | 2.96 |
| C5 acids | 0.87 |
| C6 acids | 3.74 |
| C7 esters | 0.00 |
| 2,2-dimethylpentanoic acid | 3.33 |
| 2,2,3-trimethylbutanoic acid | 0.08 |
| 2-ethyl-2-methylbutanoic acid | 79.89 |
| C8 acids | 3.86 |
| C9 acids | 2.10 |
| C10 acids | 0.70 |
| C13 acids | 2.48 |
| heavy acids | 0.00 |

The selectivity among the C$_7$ acid isomers is shown in Table 4 below.

TABLE 4

(C7 Acid Isomer Selectivity from 3M2P Concentrate)

| Component | Weight Percent |
| --- | --- |
| 2,2-dimethylpentanoic acid | 4.00 |
| 2,2,3-trimethylbutanoic acid | 0.09 |
| 2-ethyl-2-methylbutanoic acid | 95.91 |

COMPARATIVE EXAMPLE 4

This comparative example shows that when C6 olefins, other than 3M2P or 2E1B, are present, the quality of the neoacid product is unacceptable. A sample of 2-ethyl-1-butene concentrate was prepared by superfractionation from the 2-ethyl-1-butene product of the ethylene trimerization. The composition of the material, as measured by gas chromatography, is shown in Table 5 below.

TABLE 5

(Composition of 2-Ethyl-1-Butene Concentrate)

| Component | Weight Percent |
| --- | --- |
| 3-methyl-1-pentene | 0.11 |
| 1-hexene | 8.73 |
| 1,4-hexadiene | 1.86 |
| 2-ethyl-1-butene | 87.08 |
| t-2-hexene | 0.72 |

A 400 mL quantity of the 2-ethyl-1-butene concentrate was added to a 1 liter autoclave reactor. The reactor agitator was started, and the reactor was pressurized to 1300 psig ($9.0645 \times 10^6$ N/m$^2$) with carbon monoxide. Over a period of 160 minutes, 300 mL of BF$_3$•2H$_2$O were added to the reactor so that the final reactor pressure was 1500 psig ($1.03 \times 10^7$ N/m$^2$). At the end of this period, the addition of BF$_3$•2H$_2$O was stopped, and the contents were allowed to mix for another 300 minutes. During the reaction, the reactor contents were maintained at a temperature of 52° C.

At the end of 300 minutes, the reactor contents were washed with water to remove the catalyst. The resulting product had the component make-up as set forth below in Table 6.

TABLE 6

(2-Ethyl-1-Butene Concentrate Carbonylation Reactor Product)

| Component | Weight Percent |
| --- | --- |
| olefins | 5.05 |
| C5 acids | 1.01 |
| C6 acids | 3.85 |
| C7 eaters | 4.05 |
| 2,2-dimethylpentanoic acid | 4.84 |
| 2,2,3-trimethylbutanoic acid | 0.26 |
| 2-ethyl-2-methylbutanoic acid | 46.10 |
| C8 acids | 6.74 |
| C9 acids | 2.89 |
| C10 acids | 3.16 |
| C13 acids | 15.58 |
| heavy acids | 6.47 |

The selectivity among the C$_7$ acid isomers is shown in Table 7 below.

TABLE 7

(C7 Acid Isomer Selectivity from 2-Ethyl-1-Butene Concentrate)

| Component | Weight Percent |
| --- | --- |
| 2,2-dimethylpentanoic acid | 9.45 |
| 2,2,3-trimethylbutanoic acid | 0.50 |
| 2-ethyl-2-methylbutanoic acid | 90.05 |

The 2-ethyl-2-methylbutanoic acid sample produced in the present example, when distilled to remove acids of other carbon numbers, would not meet commercial specifications.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for producing 3-methyl-2-pentene which comprises the steps of:

(a) trimerizing an ethylene feedstream and/or co-dimerizing an ethylene and 1-butene feedstream at a temperature in the range between about 0° C. to about 100° C. and at a pressure sufficient to maintain said ethylene or ethylene and 1-butene in the liquid phase in the presence of a titanium-based catalyst which forms a hydrocarbon product comprising at least 2-ethyl-1-butene;

(b) separating said hydrocarbon product from said titanium-based catalyst;

(c) etherifying said hydrocarbon product by mixing said hydrocarbon product and at least one alcohol to produce an etherification mixture, and catalytically reacting said etherification mixture in the presence of an etherification catalyst under reaction conditions which form an ether-containing stream from said hydrocarbon product and said alcohol;

(d) separating an ether product from said ether-containing stream;

(e) contacting said ether product with a catalyst which is capable of decomposing said ether product to form a 3-methyl-2-pentene stream which comprises unreacted ether product; and (f) separating said alcohol of step (c) and said unreacted ether product of step (e) from said 3-methyl-2-pentene stream to form a 3-methyl-2-pentene product.

2. The method according to claim 1 wherein said temperature of step (a) is in the range between about 50° C. to about 60° C.

3. The method according to claim 1 wherein said pressure is in the range between about 0.2 to about 30 atm.

4. The method according to claim 1 wherein said titanium-based catalyst used in step (a) is obtained by reacting a mixture of alkyl titanate and ether with alkylaluminum compound.

5. The method according to claim 1 wherein the separation of hydrocarbon from said titanium-based catalyst is via absorption or distillation.

6. The method according to claim 1 wherein said etherification catalyst is ether an acid resin catalyst or a zeolite catalyst.

7. The method according to claim 6 wherein said acid resin catalyst is selected from the group consisting of: cation exchange resin catalysts and macroreticular sulfonic acid cation exchange resin catalysts.

8. The method according to claim 1 wherein the separation of said ether product from said ether-containing stream is via distillation.

9. The method according to claim 1 wherein said alcohol is methanol and said ether product is 3-methoxy-3-methylpentane.

10. The method according to claim 1 wherein said decomposition step (e) comprises contacting said ether product with at least one catalyst selected from the group consisting of: acid resin catalysts, zeolite catalysts, alumina catalysts, and clay catalysts.

11. The method according to claim 1 wherein said separation step (f) comprises extracting with water for the removal of alcohol(s) from the 3-methyl-2-pentene stream, and distilling the alcohol depleted 3-methyl-2-pentene stream to separate unreacted ether product from said 3-methyl-2-pentene stream to form said 3-methyl-2-pentene product.

12. A method for producing 2-ethyl-2-methylbutanoic acid which comprises the steps of:
(i) producing 3-methyl-2-pentene by the steps of (a) trimerizing an ethylene feedstream and/or co-dimerizing an ethylene and 1-butene feedstream at a temperature in the range between about 0° C. to about 100° C. and at a pressure sufficient to maintain said ethylene or ethylene and 1-butene in the liquid phase in the presence of a titanium-based catalyst which forms a hydrocarbon product comprising at least 2-ethyl-1-butene; (b) separating said hydrocarbon product from said titanium-based catalyst; (c) etherifying said hydrocarbon product by mixing said hydrocarbon product and at least one alcohol to produce an etherification mixture, and catalytically reacting said etherification mixture in the presence of an etherification catalyst under reaction conditions which form an ether-containing stream from said hydrocarbon product and said alcohol; (d) separating an ether product from said ether-containing stream; (e) contacting said ether product with a catalyst which is capable of decomposing said ether product to form a 3-methyl-2-pentene stream which comprises unreacted ether product; and (f) separating said alcohol of step (i)(c) and said unreacted ether product of step (i)(e) from said 3-methyl-2-pentene stream to form a 3-methyl-2-pentene product; and (ii) mixing said 3-methyl-2-pentene product together with carbon monoxide, water, and a strong acid catalyst at a temperature of about 25° C. to about 100° C. and at a pressure in the range between about 1000 psig to about 3000 psig to form 2-ethyl-2-methylbutanoic acid.

13. The method according to claim 1 wherein said temperature of step (c) is in the range between about 72° to 78° C.

14. The method according to claim 12 wherein said temperature of step (i)(c) is in the range between about 72° to 78° C.

15. The method according to claim 1 wherein step (c) has sufficient pressure to keep said hydrocarbon product and said at least one alcohol in the liquid phase.

16. The method according to claim 12 wherein step (i)(c) has sufficient pressure to keep said hydrocarbon product and said at least one alcohol in the liquid phase.

17. The method according to claim 12 wherein said titanium-based catalyst is obtained by reacting a mixture of alkyl titanate and ether with an alkylaluminum compound.

* * * * *